United States Patent [19]

Onopchenko et al.

[11] Patent Number: 5,102,569
[45] Date of Patent: Apr. 7, 1992

[54] METHOD OF PREPARING BORATED ALKYL AROMATIC POLYOLS

[75] Inventors: Anatoli Onopchenko, Concord; Thomas V. Liston, San Rafael, both of Calif.

[73] Assignee: Chevron Research and Technology Company, San Francisco, Calif.

[21] Appl. No.: 601,959

[22] Filed: Oct. 23, 1990

[51] Int. Cl.⁵ .................................. C10M 139/00
[52] U.S. Cl. ........................ 252/49.6; 568/5; 568/6
[58] Field of Search ................. 568/5, 6; 252/49.6

[56] References Cited

U.S. PATENT DOCUMENTS

| | | |
|---|---|---|
| 2,795,547 | 6/1957 | Harle et al. ............... 252/49.6 |
| 2,795,548 | 6/1957 | Thomas et al. ............ 252/49.6 |
| 3,361,672 | 1/1968 | Andress et al. ........... 252/49.6 |
| 4,629,578 | 12/1986 | Liston ..................... 252/33.4 |
| 4,701,274 | 10/1987 | Croudace et al. .............. 568/6 |
| 4,788,340 | 11/1988 | Horodysky ............... 252/49.6 |
| 4,975,211 | 12/1990 | Small, Jr. et al. ......... 252/49.6 |

Primary Examiner—Prince Willis, Jr.
Assistant Examiner—Ellen M. McAvoy
Attorney, Agent, or Firm—Richard C. Gaffney

[57] ABSTRACT

A method of preparing a borated alkylcatechol by first reacting catechol with boric acid and thereafter alkylating with an olefin.

17 Claims, No Drawings

METHOD OF PREPARING BORATED ALKYL AROMATIC POLYOLS

BACKGROUND OF THE INVENTION

1. Field of the Invention

This invention is concerned with a method of producing a borated alkyl aromatic polyol. More particularly, it relates to a method of producing a borated alkyl aromatic polyol used in lubricating oil formulations to reduce oxidation, wear, and deposits in internal combustion engines.

2. Description of the Relevant Art

Wear and deposits limit the useful life of automobile and truck engines. Thus, there is a great need to find lubricants that reduce the oxidation, wear, and deposits in the engine, thus increasing the lifetime of the engine.

U.S. Pat. No. 2,795,548 discloses the use of lubricating oil compositions containing a borated alkyl catechol. The oil compositions are useful in the crankcase of an internal combustion engine in order to reduce oxidation of the oil and corrosion and wear of the metal parts of the engine.

Borated alkyl catechols are conventionally prepared via alkylation of catechol with an olefin, followed by boration of the alkyl catechol product with boric acid or boric anhydride (see, for example, U.S. Pat. No. 4,629,578). Hereinafter this will be referred to as the "forward process". This procedure produces borated products containing both monoalkyl and dialkyl catechols; however, the superior antioxidant properties of the monoalkyl catechols make them more desirable products. To enhance the production of monoalkyl products, a large excess of catechol, the most expensive reactant in the process, is needed in the forward process. Unfortunately, this excess catechol must be recovered and recycled to make the process economical.

OBJECTS OF THE INVENTION

The present invention concerns a new process for producing borated alkyl aromatic polyols, such as borated alkyl catechols, that minimizes the need, if any, for aromatic polyol recovery and recycle procedures. In the process of this invention, the boration of the aromatic polyol precedes the alkylation of the borated aromatic polyol product. Hereinafter this will be referred to as the "reverse process". Unlike the forward process, the production of borated alkyl catechols (using catechol as an example of an aromatic polyol) containing monoalkyl catechols is enhanced in the reverse process without using excess catechol. As no catechol recycle and recovery steps are anticipated, the new reverse process simplifies the preparation of borated alkyl catechols by eliminating a distillation, or a stripping procedure, or a solvent extraction, needed in the forward process for recovery of catechol; reduces the cost of their production; and offers other advantages to be discussed below.

The present reverse process is also advantageous over the forward process because the final product has a higher content of the 4-alkyl catechol isomer than the 3-alkyl catechol isomer. The 3-alkyl catechol isomer is less desirable because it is structurally similar to natural products which possess undesirable biological activity, such as skin irritation. [A. P. Kurtz and C. R. Dawson, J. Medicinal Chemistry, Vol. 14, pp. 729 and 733 (1971)]. The results obtained via the "reverse process" are clearly unexpected. First, there is no prior art dealing with alkylation of borated aromatic polyols, including catechol borates.

All indications point to the fact that aromatic polyol borates are hydrolytically unstable and revert back to starting materials, namely aromatic polyol and boric acid, on exposure to moisture in the air [Kirk-Othmer Encyclopedia of Chemical Technology, Vol. 4, pp. 112-114 (1978); H. Steinberg and D. L. Hunter, Industrial and Engineering Chemistry, Vol. 49, 174 (1957)]. It may be for this reason that the alkylation of aromatic polyol borates apparently has not been attempted. Secondly, the literature indicates that substitution of a phenolic OH group by a methoxy ($OCH_3$) reduced the reactivity of the aromatic ring (F. A. Drahowzal, in Friedal-Crafts and Related Reactions, G. A. Olah, Editor, II, Alkylation and Related Reactions, Part I, 1964, Interscience Publishers, p. 434). For example, in the alkylation of phenol and anisole (methoxy-benzene) with tert-butyl cations, phenol was about 3-6 times more reactive than anisole (M. Attina et al., J. Chem. Soc. Chem. Commun. 466 (1976). In the alkylation of catechol and dimethoxybenzene with 2-butyl-1-octene, catechol was some 60 times more reactive than the ether (see Examples in Table 2 below). Therefore, substitution of phenolic hydroxyl groups in catechol by a borate functionality ($-O-BO_2$), i.e., converting catechol to catechol borate, was also expected to lower the reactivity of the aromatic ring in the catechol borate to alkylation. Considering that alkylation of phenolics in commercial batch operations in the "forward process" are routinely carried out for 4-12 hours, it would seem unrealistic to do anything that will increase the reaction time even further. Surprisingly, as the data presented later show, the alkylation of catechol via the "reverse process" proceeded smoothly in a reasonably length of time, along with the other advantages previously discussed.

The present process also addresses the problem of using said borated alkyl catechols of the reverse process in lubricating oils in spite of the fact that they are sensitive to moisture and hydrolyze readily. The hydrolysis leads to haze and/or precipitate formation which must be filtered out prior to use. It has now been found that said borated alkyl catechols, prepared via the reverse process, may be stabilized against hydrolysis by complexing the borated alkyl catechol with, for example, succinimides, in the same manner as previously disclosed in the "forward process" (see U.S. Pat. No. 4,629,578).

More importantly, it has now been found that lubricating the crankcase of an internal combustion engine with a lubricating oil containing the borated alkyl catechols made via the reverse process of this invention reduces oxidation and wear in gasoline engines and deposits in diesel engines.

SUMMARY OF THE INVENTION

In accordance with this invention, a new method of preparing borated alkyl aromatic polyols has been discovered which comprises first reacting certain aromatic polyols which have hydroxyl groups in vicinal (adjacent) positions on aromatic ring carbon atoms with a borating agent to produce a borated aromatic polyol and thereafter reacting the borated aromatic polyol with a monoolefin under alkylation conditions to produce the desired borated alkyl aromatic polyol.

In one preferred embodiment, a solvent is employed in the first or boration step which can azeotrope with water for ease of removal of the water of reaction from the system.

In another preferred embodiment, the borated alkyl aromatic polyols are prepared in a one-pot reaction. First, a reaction mixture comprising an aromatic polyol having hydroxyl groups in vicinal positions on aromatic carbon atoms is reacted with a borating agent to produce a borated alkyl polyol and water in the conjoint presence of a solvent which azeotropes with water and optionally at least one monoolefin having at least four carbon atoms. Water of reaction is removed from the system as an azeotrope with the solvent. An alkylation catalyst is thereafter added to the reaction mixture and the borated aromatic polyol is alkylated with the olefin already present in the mixture to produce the desired borated alkyl aromatic polyol. If desired, the olefin can be added to the reaction mixture with the catalyst after boration has been completed, especially in the case where low boiling olefins such as butenes, hexenes, and octenes are employed.

Other additives may also be present in the lubricating oils in order to obtain a proper balance of properties such as dispersancy, corrosion, wear and oxidation inhibition which are critical for the proper operation of an internal combustion engine.

In still another aspect of this invention, a method is provided for reducing wear, oxidation and deposits in an internal combustion engine by utilizing the lubricating oil composition described above. Specifically, improvements in deposits in diesel engines may be obtained by employing the composition of this invention. Improvements in viscosity control can be obtained in spark-ignition engines, that is, gasoline engines. Additionally, lubricating oil compositions containing the borated alkyl aromatic polyols of this invention have been found to possess (1) antioxidant properties in gasoline engines and (2) diesel deposit inhibition when employed in diesel engines.

DETAILED DESCRIPTION OF THE INVENTION

The present invention relates to a lubricating oil additive, containing borated alkyl aromatic polyols, prepared via the reverse process. The aromatic polyols which are useful in the present invention are aromatic polyols which have hydroxyl groups in vicinal (adjacent) positions on aromatic ring carbon atoms.

The preferred aromatic polyols have from 1 to 3 aromatic rings and from 2 to 4 hydroxyl groups and wherein at least two of the hydroxyl groups are in vicinal positions on aromatic ring carbon atoms.

Most preferably the aromatic polyol is a single ring aromatic having from 2 to 4 hydroxyl groups and wherein at least 2 of such hydroxyl groups are in vicinal positions on aromatic ring carbon atoms. Examples of suitable aromatic polyols include, but are not limited to;

1, 2-Benzenediol (Catechol) 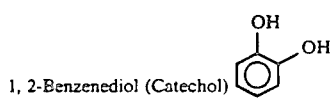

-continued 1, 2, 3-Benzenetriol (Pyrogallol) 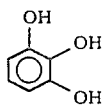

1, 2, 4-Benzenetriol (Hydroquinol) 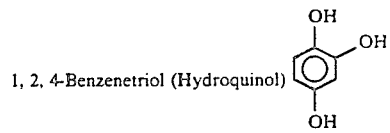

1, 2, 3, 5-Benzenetetrol 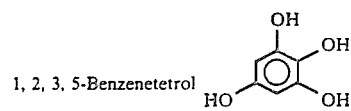

1, 2, 4, 5-Benzenetetrol 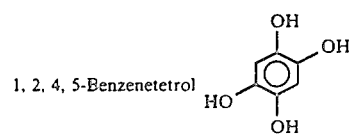

1, 2, 3, 4-Benzenetetrol (Apionol) 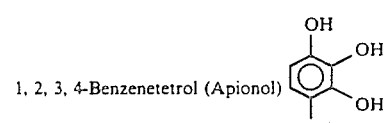

1, 2-Naphthalenediol 

2, 3-Naphthalenediol 

1, 2, 3-Naphthalenetriol (Naphthopyrogallol) 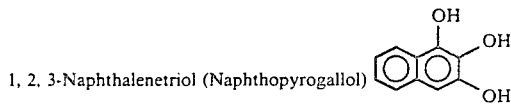

1, 2, 4-Naphthalenetriol 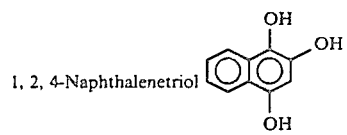

1, 2, 5-Naphthalenetriol 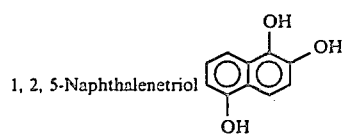

1, 2, 6-Naphthalenetriol 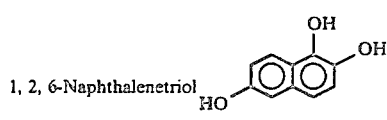

1, 2, 7-Naphthalenetriol 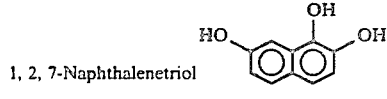

2, 3, 6-Naphthalenetriol 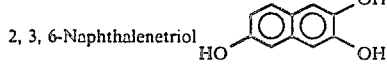

-continued 1, 2, 4, 5-Naphthalenetriol 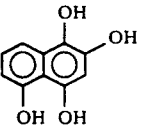

1, 2, 4, 7-Naphthalenetetrol 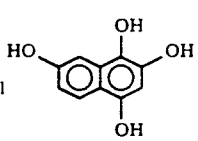

1, 2-Anthracenediol 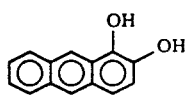

2, 3-Anthracenediol 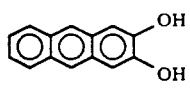

1, 2, 4-Anthracenetriol 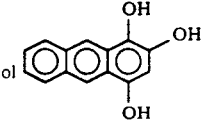

1, 2, 8-Anthracenetriol 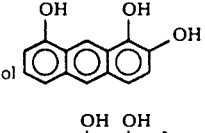

1, 2, 9-Anthracenetriol 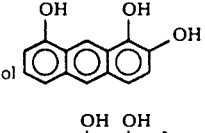

1, 2, 10-Anthracenetriol (Anthrarobin) 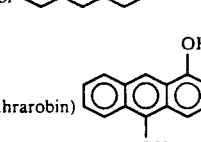

The aromatic polyol is borated with any suitable borating agent, such as boric acid or boric anhydride, under boration conditions which are well known to those skilled in the art. (See, for example, the teachings on boration in U.S. Pat. No. 4,629,578 which are incorporated herein by reference.) The boration involves preferential reaction with any two hydroxyl groups in vicinal positions on aromatic ring carbon atoms. The boration catechol is described below for illustration purposes.

Catechol borate is prepared in said boration by reacting catechol with boric acid or boric anhydride while removing the water of the reaction azeotropically. The exact structure of the catechol borate will vary, depending on the amounts of catechol and boric acid or boric anhydride used. The molar ratio of catechol to boric acid used will range from about 1:1 to 2:1, and typically will be near 1.5:1; i.e., one Boron will be added for every 2 to 4 hydroxyl groups in the aromatic polyol. If more than the stoichiometric amount of boric acid or boric anhydride is used, some of the acid will remain unreacted. Because of the insolubility in oil and the abrasive nature of the boric acid, the unreacted acid must be removed prior to using the blend in an engine. If too little boric acid or boric anhydride is used, then only partial boration can occur, the full benefit of boron additive may not be realized, and engine performance may not be at its optimum. The borated alkyl catechols may be prepared by reacting a $C_4$–$C_{40}$ olefin, such as a branched olefin or straight-chain alpha olefin containing 4 to 40 carbon atoms or mixtures thereof, with catechol borate in the presence of an acid alkylation catalyst, such as a sulfonic acid catalyst, under alkylation conditions such as a temperature from about 60° C.-200° C., preferably 100° C.-180° C., and most preferably 120° C.-150° C. in an essentially inert solvent at atmospheric or ambient pressures, although higher pressures may be needed with low boiling olefins to keep them in the liquid phase. The term "branched olefin" means that branching occurs at the double bond, i.e., vinylidene olefins or trisubstituted olefins. The term "straight-chain alpha olefin" means that the alpha olefin contains little (less than about 20%) or no branching at the double bond or elsewhere.

Although alkylation of catechol borate can be carried out neat, the use of solvents particularly in a batch reactor greatly facilitates the process due to improved mixing of the reactants, improved filtration, etc. Since solvent is generally used in the boration procedure in the preferred embodiment, it is particularly advantageous to carry out the alkylation reaction of catechol borate in the same solvent. Examples of the inert solvents include benzene, toluene, chlorobenzene and Chevron 250, 265 or 350 Thinners, which are mixtures of aromatics, paraffins and naphthenes. Other inert solvents may be used.

Borated alkyl catechol containing monoalkyl catechols are the preferred product. A product which contains predominantly monoalkyl catechol may be prepared by using appropriate molar ratios of reactants (catechol borate and alkylating olefin). Generally, when used at approximately stoichiometric molar ratios, the resulting product contains monoalkyl catechols and dialkyl catechols. A molar excess of catechol borate (e.g., two mols of catechol borate for each mol of olefin) can be used in order to enhance monoalkylation if predominantly monoalkyl catechol borates are desired. Predominantly dialkyl catechol borates may be prepared by employing a molar excess of olefin, such as two mols of the same or different olefin per mol of catechol borate. As the data shows (see Table 3 below), at a typical catechol or catechol borate/olefin ratio of 0.9:1, the reverse process produces a much higher percentage of sought after monoalkyl catechol borates.

The borated alkyl catechols in this invention are mixtures of monoalkyl and dialkyl catechols structures. The monoalkyl catechols have the preferred Formula I:

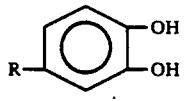

Formula I wherein R is alkyl containing 4 to 40 carbon atoms and preferably from 12 to 24 carbon atoms and more preferably 20 to 24 carbon atoms. Also, up to 60% by weight but preferably less than 50% by weight of the monoalkyl catechols may have the R group in a position adjacent or ortho to one of the hydroxy groups and have the Formula II:

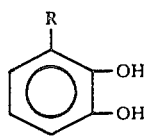

Formula II wherein R is as defined above. The dialkyl catechols are generally of Formula III:

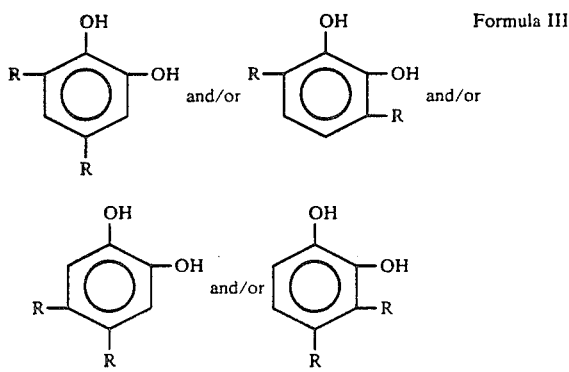

Formula III wherein R is as defined above and the two R groups can be the same or different. Trialkyl catechols may also be present although they are not preferred.

Among the alkyl catechols which may be present are hexylcatechol, octylcatechol, decyl catechol, undecyl catechol, dodecyl catechol, tetradecyl catechol, pentadecyl catechol, hexadecyl catechol, octadecyl catechol, eicosyl catechol, hexacosyl catechol, triacontyl catechol, and the like. Also, a mixture of alkyl catechols may be used, such as a mixture of $C_{14}$-$C_{18}$ alkyl catechols, a mixture of $C_{16}$-$C_{24}$ alkyl catechols, or a mixture of $C_{20}$-$C_{28}$ alkyl catechols and etc.

The borated alkyl catechols of this invention can be stabilized against hydrolysis via complexation with succinimides and added to a lubricating oil, or complexation can be carried out in situ in the lubricating oil containing the stabilizing reactant. In addition, it is contemplated that the additives of this invention can be sold as a concentrate in a neutral oil with or without other ingredients being present such as dispersants, antirust agents, and etc. When the dispersants such as succinimides are not present in the concentrate, the concentrates may require storage under a blanket of inert gas such as nitrogen to prevent hydrolysis of borated alkylcatechol in storage. In the preferred case, the concentrate can therefore comprise borated alkyl catechols, an amount of a dispersant such as succinimide, sufficient to stabilize the borated alkyl catechol against hydrolysis, and a neutral carrier oil. The weight percent of the stabilized borated alkyl catechols in the concentrate is usually from 5 to 80 based on the weight percent of neutral carrier oil, typically 10 to 60. The term "neutral oil" is well known in the art, such as those neutral oils made commercially which have a viscosity in the lubricating oil range, such as 100 neutral oils, 200 neutral oils, etc.

In general, the additives of this invention may also be used in combination with other additive agents in conventional amounts for their known purpose. For example, for application in modern crankcase lubricants, the base composition described above will be formulated with supplementary additives to provide the necessary properties of stability, detergency, dispersancy, antiwear and anticorrosion.

As another embodiment of this invention, the lubricating oils which contain the borated alkyl catechols may also contain an alkali or alkaline earth metal hydrocarbyl sulfonate, an alkali or alkaline earth metal phenate, and Group II metal salt dihydrocarbyl dithiophosphate, and conventional viscosity index improvers.

The lubricating oils used in the compositions of this invention may be mineral oils or synthetic oils of lubricating viscosity. Preferably, the lubricating oils are suitable for use in the crankcase of an internal combustion engine, having a viscosity of about 1300 cSt at 0° F. (18° C.) to 22.7 cSt at 210° F. (99° C.). The lubricating oils may be derived from synthetic or natural sources. Mineral oils suitable for use as the base oil in this invention include paraffinic, naphthenic and other oils that are ordinarily used in lubricating oil compositions. Synthetic oils include both synthetic hydrocarbon oils and synthetic esters. Useful synthetic hydrocarbon oils include liquid polymers of alpha olefins having the proper viscosity. Especially useful are the hydrogenated liquid oligomers of $C_6$-$C_{12}$ alpha olefins such as 1-decene trimer and tetramers. Likewise, alkyl benzenes of proper viscosity, such as didodecyl benzene, can be used. Useful synthetic esters include the esters of both monocarboxylic acid and polycarboxylic acids as well as monohydroxy alkanols and polyols. Typical examples are didodecyl adipate, pentaerythritol tetracaproate, di-2-ethylhexyl adipate, dilaurylsebacate and the like. Complex esters prepared from mixtures of mono and dicarboxylic acid and mono and dihydroxy alkanols can also be used.

Blends of hydrocarbon oils with synthetic oils are also useful. For example, blends of 10 to 25 weight percent hydrogenated 1-decene trimer with 75 to 90 weight percent 33 cSt at 100° F. (38° C.) mineral oil gives an excellent lubricating oil base.

Other additives which may be present in the formulation (or in the concentrate referred to above) include rust inhibitors, foam inhibitors, corrosion inhibitors, metal deactivators, pour point depressants, antioxidants, and a variety of other well-known additives.

The following examples are given to specifically illustrate the invention. These examples and illustrations are not to be construed in any way as limiting the scope of the invention.

EXAMPLE 1

Alkylation of Catechols (Forward Process)

A mixture of catechol (39.3 g) and 1-dodecene (24.0 g) in the presence of Amberlyst-15 catalyst (2.5 g) in Chevron 250 Thinner (60 ml) was heated while stirring under nitrogen for 2 hours at 140° C. in a 500-ml, three-necked, round-bottomed flask, fitted with a thermometer, a Dean-Stark trap, and a water-cooled condenser. The reaction mixture was cooled, taken up with n-hexane (250 ml), and filtered through a sintered-glass funnel to recover the catalyst. The filtrate was washed three times with 200-ml portions of water, dried over anhydrous magnesium sulfate and heated in an evaporating dish on a hot plate under a nitrogen sweep to drive off solvents. The product was analyzed by nuclear magnetic resonance spectroscopy to determine the relative amounts of 3-alkyl and 4-alkyl catechols in the product mixture, the results of which are given in Table 1.

EXAMPLE 2

Alkylation of Catechol Borate (Reverse Process)

A mixture of catechol (82.5 g), boric acid (30.9 g), and 1-dodecene (25.2 g) in Chevron 265 Thinner (150 ml) was heated while stirring under nitrogen at reflux (160° C.), while collecting water of reaction in a Dean-Stark trap. After refluxing for 3 hours, a total of 18 g of water was collected. The reaction mixture was cooled to about 110°-115° C., and Amberlyst-15 catalyst (5.8 g) was added. The reaction mixture was heated to 140° C. and held at this temperature for 8 hours with stirring. The product was filtered to recover the catalyst, and was evaporated to dryness in a rotary evaporator. Analysis of the product by infrared spectroscopy indicated that borated dodecylcatechols were formed, and that the IR spectrum of the product was similar to the spectrum of borated product prepared from alkyl catechol obtained by the procedure of Example 1. For ease of analysis, a sample was hydrolyzed to convert the borated alkylcatechol to the corresponding alkylcatechol. Analysis on a portion of the hydrolyzed product was performed by nuclear magnetic resonance spectroscopy to determine relative amounts of 3-alkyl and 4-alkyl catechols obtained from the reaction. These results are given in Table 1.

TABLE 1

| Comparison of Reaction Product Yields for Alkylation of Catechol and Catechol Borate[1] | | |
|---|---|---|
| Product | Example 1 | Example 2 |
| 3-alkyl | 57.5% | 48.8% |
| 4-alkyl | 42.5% | 51.2% |
| ratio of 3-alkyl to 4-alkyl | 1.35 | 0.95 |

[1]All product yields expressed as mol %, obtained as average of two runs, as determined by nuclear magnetic resonance spectroscopy on hydrolyzed product Table 1 shows the relative amounts of 3-alkyl and 4-alkyl catechols produced during the forward process and during the reverse process. Surprisingly, the reverse process offered a larger proportion of the sought after 4-alkyl isomer relative to the 3-alkyl isomer.

EXAMPLE 3

Alkylation of 1,2-dimethoxybenzene

A mixture of 1,2-dimethoxybenzene (3.4 g), 2-butyl-1-octene (1.0 g), and Amberlyst-15 (1.0 g) was heated in approximately 30 ml of n-decane for 4 hours at 100° C. under nitrogen. The product was isolated according to the procedure of Example 1, but omitting the water washing step, and analyzed by capillary gas-liquid chromatography (GLC) to determine the extent of olefin conversion. The results obtained are presented in Table 2.

EXAMPLE 4

By a substantially similar process, approximately 3.4 g of catechol was reacted with 1.0 g of 2-butyl-1-octene in the presence of 1.0 g of Amberlyst-15 catalyst in decane solvent at 105° C. The product was similarly analyzed by GLC to determine the extent of olefin conversion. Results are presented in Table 2.

EXAMPLE 5

By a similar procedure, catechol borate (3.4 9, 6.2% B) was reacted with 1.0 g of 2-butyl-1-octene in isooctane (30 mL) solvent in the presence of 1.0 g of Amberlyst-15 catalyst by heating under reflux (100° C.), while stirring, for 0.5 hours. The product was hydrolyzed, and the alkylcatechols formed were analyzed by GLC to determine the olefin conversion level. The results are given in Table 2.

TABLE 2

| Relative Reactivities of Catechol, Catechol Borate and 1,2-Dimethoxybenzene toward Alkylation | | | | | |
|---|---|---|---|---|---|
| Example No. | Reactant | % Olefin Conversion | Reaction Time (hrs.) | Reaction Rate (% Conv/hr) (col. 2 ÷ col. 3) | Relative Rxn. Rate[1] (col. 5 ÷ 2.5) |
| 3 | ether (1,2-dimethoxybenzene) | 10 | 4.0 | 2.5 | 1.0 |
| 4 | catechol | 74 | 0.5 | 148 | 59 |
| 5 | catechol borate | 33 | 0.5 | 66 | 26 |

[1]Reaction rate (column 5) ÷ 2.5 which is the Reaction Rate for ether.

The data in Table 2 confirms the literature predictions that alkylation of phenolics occurs much more easily than that of their substituted analogues such as ethers (1,2-dimethoxybenzene), i.e., Reaction Rate of catechol is 59 times Reaction Rate of ether. It was expected that the Reaction Rate of the catechol borate (Ex. 5) would be more like the Reaction Rate of ether (Ex. 3) since the hydroxyl groups were substituted with borate. Surprisingly, the Reaction Rate of the catechol borate was 26 times the Reaction Rate of ether albeit less than half as reactive as catechol.

EXAMPLE 6

Large-Scale Alkylation of Catechol Borate (Reverse Process)

A 20-gallon reactor was charged with catechol (4493 g), $C_{18-24}$ olefin (14,200 g), and boric acid (1681 g) in Chevron 265 Thinner solvent (8500 ml). The mixture of $C_{18-24}$ olefins was purchased from Ethyl Corporation and had the following composition: $C_{16}=2\%$; $C_{18}=5.5\%$; $C_{20}=39.5\%$; $C_{22}=36.2\%$; and $C_{24}=16.8\%$. The NMR analysis showed 5% vinylidene; 40% trisubstituted (both of these are branched olefins); and 15% vinyl and 40% internal olefins (both of these are linear). The reaction mixture was heated while stirring at reflux (150° C.), collecting water of reaction in a trap (approximately 1500 g). After reacting for 4 hours, water formation ceased, and the reaction mixture was cooled to 100° C. After adding 935 g of Amberlyst-15 catalyst, the reaction mixture was reheated to 145°-150° C., and the alkylation reaction was carried out for 12 hours. The solvent was stripped by heating to a temperature of 150° C. under a 50 mm Hg vacuum, and the catalyst was separated from the product by hot (100° C.) filtration through a Celite 512 bed in a Buchner funnel under a blanket of nitrogen. The product (17,125 g) was a dark amber oil containing 1.36% B, had a 100° C. viscosity of 21.4 cSt, and a sediment level of 0.01 vol. %. A 5.0-g sample of the hydrolyzed product was analyzed by gas-liquid chromatography for the relative yield of mono- and dialkylated products, the results of which are reported in Table 3.

EXAMPLE 7

Alkylation of Catechol
(Forward Process)

Similarly, by applying the same general procedures as outlined in Example 1, catechol and $C_{18-24}$ olefins (purchased from Ethyl Corporation—as in Example 6 above) were reacted in a 0.9/1.0 mol ratio of catechol/olefin. The product obtained by such a reaction was analyzed by GLC to determine the relative yield of mono- and dialkylated products, the results of which are reported in Table 3.

TABLE 3

| | Product Yields for Alkylation of Catechol/Catechol Borate | | | |
|---|---|---|---|---|
| Example | Species Alkylated | Catechol/Olefin Ratio | Wt. % Monoalkyl | Wt. % Dialkyl |
| 6 | catechol borate | 0.9/1.0 | 80[1] | 20[1] |
| 7 | catechol | 0.9/1.0 | 66 | 34 |

[1] As determined from GLC analysis of hydrolyzed product.

Comparing the results of the forward process (Example 7) with that of the reverse process (Example 6), clearly shows that at a given molar ratio of catechol to olefin, there is a greater proportion of the desired monoalkylated product formed in the reverse process.

EXAMPLES 8-10

Alkylation of Catechols at Varying Reactant Mole Ratios

Similarly, by applying the same general procedures as outlined in Example 7, catechol and $C_{18-24}$ olefins (again the same as in Examples 6 and 7 above) were reacted in a variety of reactant mole ratios of catechol/olefin. The products obtained by such reactions were analyzed by GLC to determine the relative yield of mono- and dialkylated products, the results of which are reported in Table 4.

TABLE 4

| | Product Yields for Alkylation of Catechol | | |
|---|---|---|---|
| Example No. | Catechol/Olefin Mole Ratio | Wt. % Monoalkyl | Wt. % Dialkyl |
| 7 | 0.9/1.0 | 66 | 34 |
| 8 | 5.0/1.0 | 98 | 2 |
| 9 | 2.0/1.0 | 84 | 16 |
| 10 | 0.4/1.0 | 22 | 78 |
| 6[2] | 0.9/1.0 | 80[1] | 20[1] |

[1] As determined from GLC analysis of hydrolyzed product.
[2] As alkylation of catechol borate (reverse procedure).

The data in Table 4 demonstrate the economic advantage of using the reverse process (Example 6) over the conventional process (Examples 7, 8, 9, and 10). For example, by using a 5/1 molar ratio of reactants (Example 8), a high yield of monoalkylated catechol was obtained, but 80% of catechol charged remained unreacted (assuming 100% reaction of the olefin) and needed to be recovered for recycle. At a molar ratio of 2/1 (Example 9), the product was still predominantly monoalkylated (84%), but about 50% of catechol remained unreacted (again assuming 100% olefin reaction). In the reverse process (Example 6), at essentially an equimolar ratio of reactants, the predominant monoalkylation occurred to the extent of about 80%, but there was no unreacted catechol present which would require recovery and recycling. Thus the reverse process offers a significant processing advantage over the forward process.

EXAMPLES 11-16

Oxidator Bench Testing

A series of runs were carried out in an oxidation bench test on fully formulated lubricating oils containing varying amounts of mono- and dialkylated catechol borates, 3.5% dispersant, 50 mmol/kg calcium as sulfonates, 17 mmol/kg zinc dialkyl dithiophosphate, and 6.8% viscosity index improver in Chevron 100N base oil. The oxidation test employed herein measures the resistance of the test sample to oxidation using pure oxygen with a Dornte-type oxygen absorption apparatus [R. W. Dornte, "Oxidation of White Oils," *Industrial and Engineering Chemistry*, 28, p. 26 (1936)]. The conditions are: an atmosphere of pure oxygen exposed to the test oil, an oil temperature of 340° F., and an oxidation catalyst comprised of 0.69% Cu, 0.41% Fe, 8.0% Pb, 0.35% Mn, and 0.36% Sn (as naphthenates) in the oil [J. Amer. Soc. Lubr. Eng., Vol. 37, p. 722, (1981), Test 1H]. The time required for 100 g of the test sample to absorb 1.0 L. of oxygen is measured.

The product tested in Example 11 was prepared via conventional boration (alkylcatechol/boric acid mole ratio 3:2) of alkylcatechol of Example 9, which employed a catechol/olefin mole ratio of 2/1. The product in Example 12 was also prepared via conventional boration (alkylation/boric acid mole ratio 3:2) of dialkylcatechol of Example 10, which employed a catechol/olefin mole ratio of 0.4/1. Examples 13, 14, and 15 represent blends of the above two products, and Example 16 is a reference run containing no added antioxidant. By plotting the composition of monoalkylcatechol in a sample from 0 to 100% against time needed to absorb 1.0 liter of oxygen, a straight line relationship was observed. Extrapolating to 100% monoalkylcatechols content and 100% dialkylcatechols content (0% monoalkylcatechols) gave extrapolated values of 21 4 hrs. for the mono-, and 13.9 hrs. for the dialkylcatechol, respectively. The results are summarized in Table 5.

TABLE 5

| Oxidator Bench Test Results on Borated Alkyl Catechols[1] | | | | | |
|---|---|---|---|---|---|
| Example No. | Borated Additive | Composition of Alkylcatechol[2] % mono | % di | Time (hrs) | Time Improvement (hrs) |
| — | — | 100 | 0 | 21.4[3] | 10.5 |
| 11 | Ex. 9 | 84 | 16 | 20.4 | 9.5 |
| 12 | Ex. 10 | 22 | 78 | 14.4 | 3.5 |
| 13[5] | — | 60 | 40 | 18.4 | 7.5 |
| 14[5] | — | 53 | 47 | 17.9 | 7.0 |
| 15[5] | — | 30 | 70 | 15.4 | 4.5 |
| — | — | 0 | 100 | 13.9[3] | 3.0 |
| 16[4] | — | 0 | 0 | 10.9 | 0.0 |

[1] Final oil blend contained 200 ppm Boron.
[2] Borated alkylcatechol to boric acid 3:2 molar ratio.
[3] Extrapolated values
[4] Reference oil
[5] Blends of additive from Examples 9 & 10.

Examination of the data in Table 5 clearly shows that all borated alkylcatechol compositions possess antioxidant properties when compared to a reference oil. The monoalkylated borated catechols, however, were far more effective antioxidants than the dialkylated borated catechols by a factor of about 3.5 (10.5/3.0). This means that in order to obtain comparable results with both the borated mono and the borated dialkylcatechols, it will require the use of more than three times as much of the borated dialkylated product than that of the borated monoalkylated product.

Other data in the Table show that the effectiveness of antioxidant properties can be broken down into categories depending on the borated monoalkylcatechol content of the additive. For example, the most effective antioxidants were those containing between 70 and 100% of borated monoalkylcatechols, which showed improvement in antioxidancy over the reference of between 8 and 10.5 hours; the moderately effective antioxidants, containing between 40 and 70% borated monoalkylcatechols, were better than the reference by some 5 to 8 hours; and the least effective antioxidants were those having 0 to 40% of borated monoalkylcatechols, showing improvement in antioxidancy over the reference of only between 3 to 5 hours.

Thus, when one considers the treat level of additives prepared by the method of this invention in a lubricating oil formulation, the difference in molecular weights of borated mono and dialkylated catechols, and their antioxidancy, the economics of using the reverse process to prepare borated alkylcatechols becomes extremely attractive.

The data in Table 5 illustrate that the most effective and thus the most desirable catechol is the borated monoalkyl catechol for antioxidant purposes. As was shown earlier, the preparation of borated alkyl catechols by the reverse process of this invention results in a product having a greater proportion of the desired monoalkyl catechol at a 1:1 catechol to olefin charge ratio.

EXAMPLES 17-21

Diesel Engine Runs

A series of engine runs were carried out which demonstrate the improvements in deposit control in a diesel engine by adding additives prepared according to Example 6.

The diesel engine runs were carried out in a single cylinder Caterpillar engine for a period of 60 hours according to 1G2 specification, using a formulation containing a diesel deposit inhibitor prepared according to the procedure of Example 6, 2.6% dispersant, 10 mmol/kg calcium phenate, 9 mmol/kg calcium sulfonate, 10 mmol/kg overbased calcium sulfonate, and 8 mmol/kg secondary zinc dialkyldithiophosphate in Cit-Con 350N base oil. For comparison, the reference runs were carried out under identical conditions, in the same engine stand, using the above formulation, but without the added deposit inhibitor. The results are shown in Table 6.

TABLE 6

| | 1G2 Diesel Engine Test Results | | | | |
|---|---|---|---|---|---|
| Example Number | Additive | Additive Conc., Wt. % | TGF[1] | TGF % Reduction[5] | WTD[2] |
| 17 | None | Reference[3] | 78(11)[4] | | 259(62) |
| 18 | Ex. 6 | 2 | 45 | | 243 |
| 19 | Ex. 6 | 2 | 18 | | 128 |
| 20 | Ex. 6 | 2 | 44 | | 335 |
| 21 | Ex. 6 | 2 | 47 | | 276 |
| | | | 39(14) | 50 | 246(87) |

TABLE 6-continued

| | 1G2 Diesel Engine Test Results | | | | |
|---|---|---|---|---|---|
| Example Number | Additive | Additive Conc., Wt. % | TGF[1] | TGF % Reduction[5] | WTD[2] |
| | | | Avg. | | Avg. |

[1]TGF = top groove fill.
[2]WTD = weighted total demerits.
[3]Results are an average of 24 reference runs carried out over 9 months using the same formulation and the same engine stand.
[4](Standard deviation).
[5]78 less 39 = 39 ÷ 78 × 100 = 50%

The engine test results clearly show the effectiveness of antioxidants, prepared via the reverse process, in reducing the deposit formation in the engine. An average of 50% reduction in TGF is obtained and this was shown to be statistically significant at the 95% confidence level.

EXAMPLE 22

Preparation of Borated Alkylcatechol from $C_{20}$-$C_{24}$ Olefin via Reverse Process A mixture of catechol (33 g), boric acid (12.4 g), and Chevron $C_{20}$-$C_{24}$ olefin mixture (99 g) was heated at reflux, while stirring, in Chevron 225 thinner solvent (100 ml) for 3 hours, collecting a total of 8.0 g of water in a Dean-Stark trap. [The Chevron $C_{20-24}$ olefin had the following composition: $C_{18}$=1%; $C_{20}$=49%; $C_{22}$=42%; and $C_{24}$=8%. The NMR analysis (% olefin types, was as follows: Branched, 40% (vinylidene); Linear, 60% (95% alpha-olefin and 5% internal olefin). The reaction mixture was cooled to about 100° C., Amberlyst-15 catalyst (7.0 g) was added, and the alkylation was carried out at 150° C. for a total of 8 hours. The product was cooled, diluted with additional thinner solvent (200 ml), and the catalyst was separated from the product by filtration through a Celite bed. The product was stripped of solvent by heating up to 135° C. at 20 mm Hg for about 45 minutes. A total of 130 g of dark amber oil was recovered, containing 1.2% B. Exposure of a small sample of product to atmospheric moisture led to development of a gelatinous film on the surface, which became a white crust on further standing for several minutes, indicative of boric acid formation.

This Example 22 is an example of the reverse process using a preferred olefin mixture.

EXAMPLE 23

Preparation of Borated Alkyl Pyrogallol from $C_{18-24}$ Olefin via Reverse Process A mixture of pyrogallol (189 g), boric acid (93 g), and $C_{18-24}$ olefin mixture (516 g) in Chevron 250 Thinner (260 mL) was heated under nitrogen while stirring at reflux (~135°-140° C.) for 10 hours, collecting a total of 67 g of water in a Dean-Stark trap. The mixture was cooled to ~100° C., and Amberlyst-15 (~5% of the total wt., 36 g) was added. The reaction mixture was then heated at 150° C. for 10.5 hours. The product was stripped under vacuum of solvent, and filtered, to give 669 g of reddish-brown viscous oil containing 2.17% of boron. The sample was stored under nitrogen.

Example 23 is an example of a different type of aromatic charge material and the one-pot technique.

EXAMPLES 24-25

Diesel engine test runs similar to those in Examples 17-21 above were run except using the borates alkyl-pyrogallol prepared in accordance with Example 23. The results are summarized in Table 7 below.

TABLE 7

1G2 Diesel Engine Test Results

| Example Number | Additive | Additive Conc., Wt. % | TGF[1] | TGF % Reduction[5] | WTD[2] |
|---|---|---|---|---|---|
| 17 | None | Reference[3] | 78(11)[4] |  | 259(62) |
| 24 | Ex. 23 | 2.0 | 60 |  | 319 |
| 25 | Ex. 23 | 2.0 | 35 |  | 309 |
|  |  |  | 48(18) Avg. | 40% | 314(7) Avg. |

[1]TGF = top groove fill
[2]WTD = weighted total demerits.
[3]Results are an average of 24 reference runs carried out over 9 months using the same formulation and the same engine stand
[4](Standard deviation)
[5]78 less 48 = 30 ÷ 78 × 100 = 40%

The results show that borated alkylpyrogallols, prepared via the reverse process, are just as effective deposit inhibitors in the engine as the corresponding borated alkylcatechols. (See Table 6 above).

EXAMPLE 26

Preparation of Borated Alkylnaphthalenediol Via Reverse Process

A mixture of 2,3-naphthalenediol (37.3 g) and boric acid (9.6 g) was heated under reflux in toluene solvent (300 mL) for 6 hours, until water of reaction stopped being formed. The mixture was evaporated to dryness in a rotary evaporator to give 39.7 g of white solid naphthalenediol borate. When the solubility of naphthalenediol borate in a lubricating oil was shown to be low, the borate was alkylated with 1-dodecene. For this purpose, a mixture of naphthalenediol borate prepared above (19.6 g), 1-dodecene (19.9 g), and Amberlyst-15 catalyst (1.0 g) was heated at reflux in chlorobenzene solvent (400 ml) for 5 hours at 135° C. The reaction mixture was filtered to separate the catalyst, and the filtrate was evaporated to dryness in a rotary evaporator to give 45 g of yellow, oily product. On standing overnight in a hood, under a flow of nitrogen, a total of 38 g of borated dodecylnaphthalenediol product was recovered, which showed much improved solubility in a lubricating oil. IR analysis showed that desired alkylation has occurred.

EXAMPLE 27

Alkylation of Catechol in the Presence of a Borating Agent

A mixture of catechol (20.1 g), $C_{14-18}$ Chevron olefin [$C_{14}$=2%; $C_{15}$=30%; $C_{16}$=30%; $C_{17}$=28%; $C_{18}$=10%; 89% vinyl olefins] fraction (45.7 g), boric acid (7.5 g), and Amberlyst-15 (5.4 g) was heated under reflux in a mixture of Chevron 225 thinner and chlorobenzene (60 and 50 mL, respectively). The water of reaction started to appear in a Dean-Stark trap on reaching 105° C., and a total of 6.8 g was collected on reaching 133° C. in a course of 3.5 hours. Filtration to separate the catalyst and evaporation of the filtrate to dryness in a rotary evaporator at 100° C. and 1 mm Hg afforded 66.1 g of product, containing 1.69% boron. Exposure of a small sample to atmospheric moisture led to formation of white crust on the surface of the sample, typical of boric acid formation. Measurement of the ratio of 3-alkylcatechols to that of 4-alkylcatechols on a hydrolyzed sample by proton nuclear magnetic resonance gave a ratio of about 62.5/37.5. Since this ratio is close to the 57.5/42.5 ratio obtained in the normal alkylation procedure of catechol (see Example 1; Table 1), it must be concluded that in the presence of boric acid and Amberlyst catalyst together at the beginning of the reaction, the first reaction to occur is the alkylation reaction of catechol, and boration of alkylated catechol occurs only on prolonged heating at reflux when sufficient amount of water has been removed.

It then becomes clear that in order to realize the various advantages observed in the reverse process, every effort should be made to ensure that required boration is completed before alkylation is attempted. In this application, the above requirement is achieved by adding the alkylation catalyst to the reaction mixture only after the boration reaction had been completed. Another way of meeting the above requirement is to add olefin to the reaction mixture after boration has been completed. If desired, the olefin and the alkylation catalyst can both be added at the same time after boration reaction has been completed.

Stabilizing agents are frequently added to borated polyols. In general, borated alkyl aromatic polyols are readily hydrolyzed by moisture. This hydrolysis results in the formation of an undesirable precipitate and/or haze which must be removed by filtration prior to use. It has now been found that the borated alkyl aromatic polyols prepared by the method of the present invention can be stabilized against hydrolysis by complexation with a suitable amine. Suitable amines include those amines known in the art to stabilize borates prepared by the forward process, such as the succinimides described in U.S. Pat. No. 4,629,578 and aliphatic amines, such as diethyl amine described in U.S. Ser. No. 375,784. In general, the amine stabilizing agent will be used in an amount sufficient to provide a borated alkyl aromatic polyol-amine complex which does not "skin-over" or form a precipitate, due to hydrolysis of the borated alkyl aromatic polyol, when stored at room temperature ($\sim$20° to 25° C.) and ambient humidity for at least one week, preferably three months.

EXAMPLE 28

Diethylamine Stabilization of Alkylated Catechol Borate

An alkylated catechol borate of Example 6 (600g, 1.36% B) was charged into a 2-liter, three-necked, round-bottomed flask fitted with a stirrer, thermometer, a condenser, and a dropping funnel. The catechol borate was warmed to about 30°-35° C., and while stirring, diethylamine (55g) was incrementally added over a 1 hour period, maintaining a temperature during addition below the boiling point of the amine. When amine addition was completed, the mixture was heated to 115°-125° C., and reaction was continued for an additional 1 hour to give 621 g of dark amber, viscous oil, A sample of product when exposed to atmospheric moisture in a petri dish, showed no haze or precipitate formation on standing for 2 weeks, indicating that successful stabilization had taken place. Infrared spectrum of this product was essentially similar to the spectrum of diethylamine stabilized product prepared by the forward process.

EXAMPLES 29-34

Gasoline Engine Runs

A series of Examples were carried out which demonstrate the improvements in oxidation and wear obtained by adding lubricating oil compositions of this invention to the crankcase of a gasoline automobile engine using additives prepared in accordance with Example 6 and stabilized with diethylamine in accordance with Example 28.

In these Examples a 350 CID Oldsmobile engine was run on a dynamometer. An engine oiling system was devised in order to provide proper lubrication to the engine and also to provide the capability to change the oil without stopping the engine. Basically, a dry sump system was used with an external pump providing lubrication to the engine. This pump was connected through valves to four external sumps. The positioning of the valves determined the oil used. The gasoline engine runs were carried out in an eight-cylinder Oldsmobile engine for a period of 64 hours according to Sequence IIID specifications. The formulation contained a known concentration of oxidation inhibitor of this invention to be tested, 3.5% dispersant, 45 mmol/kg mixed calcium and magnesium sulfonates, 13 mmol/kg mixed zinc dialkyldithiophosphates, 10% viscosity index improver (ethylene propylene copolymer) in Chevron 100N/240N base oils, formulated to SAE 5W-30 grade. The reference runs (Examples 15-16 below) were carried out under identical conditions, using the same engine stand, using the above formulation, but containing no oxidation inhibitor, i.e., without using the stabilized borated alkyl catechols of this invention. The results of the Examples are summarized in Table 8 below.

TABLE 8

Sequence IIID Engine Test Results

| Example No. | Additive | Additive Conc., wt % | Hours to 375% Viscosity Increase | Average Cam & Lifter Wear (mils[1]) |
|---|---|---|---|---|
| 29 | reference | — | 24.2 | 3.3 |
| 30 | reference | — | 30.7 27.5(4.6)[2] Avg. | 1.4 2.4(1.3) Avg. |
| 31 | Ex. 28 | 0.55 | 47.1 | 3.1 |
| 32 | Ex. 28 | 0.55 | >40 43.6(5.0) Avg. | 1.9 2.5(0.8) Avg. |
| 33 | Ex. 28 | 0.82 | 56.1 | 4.0 |
| 34 | Ex. 28 | 0.82 | 52.1 54.1(2.8) Avg. | 2.2 3.1(1.3) Avg. |

[1] passing specification = 4.0 mils or less
[2] (standard deviation)
[3] product stabilized with diethylamine The Sequence IIID engine test requires 64 hours to reach a maximum of 375% increase in viscosity to pass the oxidation part of the test. Referring to Table 8 above, the reference oil (Examples 29 & 30) required only 27.5 hours to achieve the 375% increase, i.e., the reference oil oxidized rapidly. Examples 31 through 34 show that the addition of the Example 28 additive improves the oxidation stability of the oil, i.e., the addition of 0.55 weight percent additive improves the oxidation stability of the oil to 43.6 hours while the addition of 0.82 weight percent further improves the oxidation stability to 54.1 hours. Extrapolation of the above indicates about 1% of the Example 28 additive would provide sufficient oxidation stability to pass the Sequence IIID test. Other data in the Table 8 (last column) for Examples 29-34 shows that all engine runs passed the required wear part of the test with the average wear in all cases being well below the accepted 4 mils specification.

Applicants are not intended to be limited in their invention to the foregoing examples but only to the appended claims.

What is claimed is:

1. A method of preparing a borated alkyl aromatic polyol which comprises:
   (a) reacting an aromatic polyol having from 1 to 3 aromatic rings and from 2 to 4 hydroxyl groups and wherein at least two of said hydroxyl groups are in vicinal positions on aromatic ring carbon atoms with a borating agent under boration conditions to produce a borated aromatic polyol and thereafter;
   (b) reacting said borated aromatic polyol with a monoolefin under alkylation conditions to produce said borated alkyl aromatic polyol.

2. A method according to claim 1 wherein the borating agent is boric acid.

3. A method according to claim 1 wherein the aromatic polyol is a single ring aromatic having from 2 to 4 hydroxyl groups and wherein at least two of such hydroxyl groups are in vicinal positions on aromatic ring carbon atoms.

4. A method according to claim 1 wherein the monoolefin is at least one olefin having from 4 to 40 carbon atoms.

5. A method according to claim 4 wherein the monoolefin is at least one olefin having 12 to 24 carbon atoms.

6. A method according to claim 3 wherein the aromatic polyol is catechol.

7. A method according to claim 3 wherein the aromatic polyol is pyrogallol.

8. A method according to claim 3 wherein the aromatic polyol is 2,3-naphthalenediol.

9. A method according to claim 6 wherein the borating agent is boric acid and the monoolefin is a mixture of olefins having from 12 to 24 carbon atoms.

10. A method of preparing a lubricating oil composition which comprises:
    (a) reacting an aromatic polyol having from 1 to 3 aromatic rings and from 2 to 4 hydroxyl groups and wherein at least two of said hydroxyl groups are in vicinal positions on aromatic ring carbon atoms with a borating agent under boration conditions to produce a borated aromatic polyol and thereafter;
    (b) reacting said borated aromatic polyol with a monoolefin under alkylation conditions to produce a borated alkyl aromatic polyol;
    (c) separating said borated alkyl aromatic polyol; and
    (d) admixing an antioxidant amount of said borated alkyl aromatic polyol with a lubricating oil base stock to produce said lubricating oil composition.

11. A method according to claim 10 wherein the aromatic polyol is catechol.

12. A method according to claim 11 wherein the borating agent is boric acid and the monoolefin is a mixture of olefins having from 12 to 24 carbon atoms.

13. A method according to claim 12 wherein the mixture of olefins has from 20 to 24 carbon atoms.

14. A method according to claim 1 wherein said aromatic polyol is reacted with said borating agent in the added presence of a solvent which azeotropes with water; reacting said aromatic polyol with said borating agent while continuously removing an azeotrope of said solvent and water; separating said water and recycling said solvent.

15. A one-pot method for preparing a borated alkyl aromatic polyol which comprises:

(a) reacting a first mixture comprising an aromatic polyol having from 1 to 3 aromatic rings and from 2 to 4 hydroxyl groups on aromatic ring carbon atoms with a borating agent to produce a borated aromatic polyol and water in the conjoint presence of a solvent which azeotropes with water and at least one monoolefin having at least four carbon atoms;

(b) removing an azeotrope of said solvent and the water of reaction; and (c) thereafter adding to said reaction mixture an alkylation catalyst and alkylating said monoolefin with said borated aromatic polyol to produce said borated alkyl aromatic polyol.

16. A method according to claim 15 wherein said aromatic polyol is catechol and said borating agent is boric acid 17. A method according to claim 16 wherein the water of reaction is separated and the solvent is recycled to the reaction mixture.

* * * * *